United States Patent

Rüegg

[11] Patent Number: 5,965,486
[45] Date of Patent: Oct. 12, 1999

[54] HERBICIDAL COMPOSITION AND METHOD OF WEED CONTROL

[75] Inventor: Willy Rüegg, Gipf-Oberfrick, Switzerland

[73] Assignee: Novartis Crop Protection, Inc., Greensboro, N.C.

[21] Appl. No.: 09/091,328

[22] PCT Filed: Dec. 23, 1996

[86] PCT No.: PCT/EP96/05829

§ 371 Date: Oct. 15, 1998

§ 102(e) Date: Oct. 15, 1998

[87] PCT Pub. No.: WO97/24930

PCT Pub. Date: Jul. 17, 1997

[30] Foreign Application Priority Data

Jan. 4, 1996 [CH] Switzerland ............... 18/96

[51] Int. Cl.⁶ .............................................. A01N 57/100
[52] U.S. Cl. .............................................. 504/128
[58] Field of Search ............................................. 504/128

[56] References Cited

U.S. PATENT DOCUMENTS

| | | | |
|---|---|---|---|
| 4,885,023 | 12/1989 | Yamaguchi et al. | 71/90 |
| 4,906,279 | 3/1990 | Yamaguchi et al. | 71/90 |
| 4,971,908 | 11/1990 | Kishore et al. | 435/172.1 |
| 5,145,783 | 9/1992 | Kishore et al. | 435/320.1 |
| 5,188,642 | 2/1993 | Shah et al. | 47/58 |
| 5,273,894 | 12/1993 | Strauch et al. | 435/129 |
| 5,276,268 | 1/1994 | Strauch et al. | 800/205 |
| 5,637,489 | 6/1997 | Strauch et al. | 435/172.3 |

FOREIGN PATENT DOCUMENTS

| | | |
|---|---|---|
| 0 242 236 | 10/1987 | European Pat. Off. . |
| 0 242 246 | 10/1987 | European Pat. Off. . |
| WO 86/02097 | 4/1986 | WIPO . |
| WO87/05627 | 9/1987 | WIPO . |

Primary Examiner—Jose' G. Dees
Assistant Examiner—Alton Pryor
Attorney, Agent, or Firm—Michael P. Morris; William A. Teoli, Jr.; John D. Peabody, III

[57] ABSTRACT

The invention relates to a herbicidal composition, comprising a compound of formula I

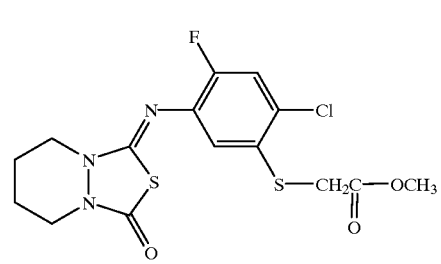

and a compound of formula II

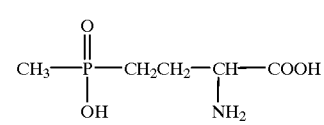

and/or of formula III

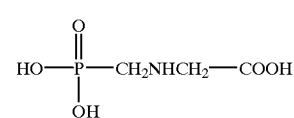

or an agriculturally acceptable salt of the compound of formula II and/or III in admixture.

9 Claims, No Drawings

HERBICIDAL COMPOSITION AND METHOD OF WEED CONTROL

This is a 371 of PCT/EP/96/05489, Dec. 7, 1996.

The present invention relates to a novel herbicidal composition that contains a combination of herbicides suitable for selectively controlling weeds in crops of cultivated plants, typically in crops of cereals, rape, sugar beet, sugar cane, plantations, rice, cotton and, preferably, in crops of maize and soybean.

The invention further relates to a method of controlling weeds in crops of cultivated plants and to the use of said novel composition therefor. The compound of formula I

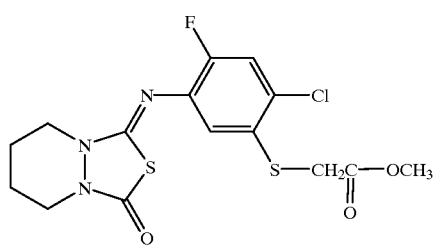

has herbicidal action. This is disclosed, inter alia, in EP-A-0 273 417.

The following compounds of formulae II and III

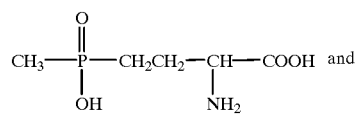

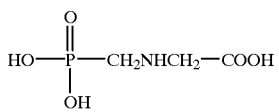

as well as their agriculturally acceptable salts, in particular the alkali metal salts, ammonium salts and amine salts, are also known as herbicides (glufosinate and glyphosate) and are described, inter alia, in "The Pesticide Manual", Tenth Edition 1994, Crop Protection Publications, and they are also commercially available.

Surprisingly, it has now been found that a combination of an active compound of formula I with one of the above herbicides of formula II and/or III, in a varying ratio, exerts a herbicidal effect that is able to control the majority of weeds occurring in particular in crops of cultivated plants preemergence as well as, preferably, postemergence without substantial injury to the cultivated plant.

Accordingly, the present invention provides a novel composition for selectively controlling weeds, which comprises, as active ingredient, a compound of formula I

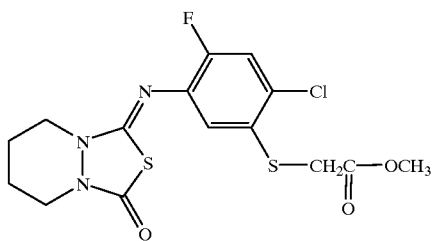

and a compound of formula II

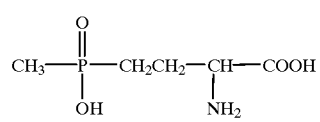

and/or of formula III

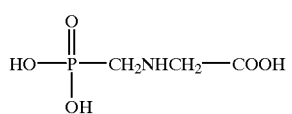

or an agriculturally acceptable salt of the compound of formula II and/or III in admixture.

Suitable salt formers for the compounds of formulae II and III are amines, ammonium hydroxide as well as alkali metal hydroxides and alkaline earth metal hydroxides.

Illustrative examples of amines suitable for salt formation are primary, secondary and tertiary aliphatic and aromatic amines, typically methylamine, ethylamine, propylamine, isopropylamine, the four isomeric butylamines, dimethylamine, diethylamine, diethanol-amine, dipropylamine, diisopropylamine, di-n-butylamine, pyrrolidine, piperidine, morpholine, trimethylamine, triethylamine, tripropylamine, quinuclidine, pyridine, quinoline and isoquinoline, in particular ethylamine, propylamine, diethylamine or triethylamine, preferably isopropylamine and diethanolamine.

Typical examples of quaternary ammonium bases are generally the cations of halo-ammonium salts, typically the tetramethylammonium cation, trimethylbenzyl-ammonium cation, triethylbenzylammonium cation, tetraethylammonium cation, trimethylethyl-ammonium cation, and also the ammonium cation.

The novel herbicidal combination can be used against a great number of agriculturally important weeds in crops of cultivated plants, in particular in crops of maize and soybean, including Veronica, Galium, Papaver, Solanum, Chenopodium, Amaranthus, Xanthium, Abutilon, Ambrosia, Sagitaria, Ipomoea, Cassiastora, *Datura stramonium, Sesbania exaltata* and *Sida spinosa.*

The novel compositions are suitable for all standard methods of application used in agriculture, typically preemergence application, postemergence application, which is preferred, and seed dressing.

The novel herbicidal combination is preferably suitable for weed control in crops of cultivated plants, typically cereals, rape, sugar beet, sugar cane, plantations, rice, cotton and, preferably, maize and soybean.

Crops will be understood as meaning also those crops that have been made tolerant to herbicides or classes of herbicides by conventional breeding or genetic engineering methods, e.g. to glyphosate or glufosinate, in particular crops of soybean and maize tolerant to glyphosate and glufosinate.

Crops of cultivated plants which are tolerant to the components of formula II and/or III are preferably prepared by biotechnological methods. The methods for the preparation of such plants which are tolerant to the compounds of formula II and/or III are described in detail in the international applications WO 86/02097 and WO 87/05627, in the European applications EP-A 242 236, EP-A 242 246, EP-A 257 542 and EP-A 275 957 and in U.S. Pat. No. 5,188,642, U.S. Pat. No. 4,971,908 and U.S. Pat. No. 5,145,783 (EPSP synthase) and form part of the present application by reference.

The novel herbicidal combination comprises the compound of formula I and the compound of formula II and/or III in any mixing ratio, one component usually exceeding the other. Preferred mixing ratios between the compound of formula I and the components of formula II and/or III are normally from 1:20 to 1:5.

The novel compositions preferably comprise the compound of formula I and the compound of formula II or III.

The rate of application can vary over a wide range and will depend on the nature of the soil, the type of application (pre- or postemergence), seed dressing, application to the seed furrow; no tillage application etc.), the cultivated plant, the weed to be controlled, the respective prevailing climatic conditions; and on other factors governed by the type of application, time of application and the target crop. The novel herbicidal combination can be usually be applied in a rate of application of 250 to 2500 g/ha, preferably of 500 to 1000 g/ha.

The weight ratio of the compound of formula I to the compound of formula II and/or III in the novel formulation is from 1:100 to 1:0.001.

The herbicidal combinations of the compound of formula I with the herbicides of formula II and/or III may be used in unmodified form, i.e. as obtained in the synthesis, but preferably they are processed in conventional manner with the assistants customarily employed in formulation technology to directly sprayable or dilutable solutions, dilute emulsions, wettable powders, soluble powders, dusts, granulates or microcapsules. As with the type of compositions, the methods of application such as spraying, atomising, dusting, wetting, scattering, or pouring, are chosen in accordance with the intended objectives and the prevailing circumstances.

The formulations, i.e. the compositions containing the compounds of formulae I and II and/or III and usually one or more than one solid or liquid formulation assistant, are prepared in known manner, e.g. by homogeneously mixing and/or grinding the herbicide with said formulation assistants, typically solvents or solid carriers. Surface-active compounds (surfactants) may additionally be used for preparing the formulations.

Suitable solvents may typically be: aromatic hydrocarbons, preferably the fractions containing 8 to 12 carbon atoms such as mixtures of alkylbenzenes, typically xylene mixtures or alkylated naphthalenes; aliphatic and cycloaliphatic hydrocarbons such as paraffins, cyclohexane or tetrahydronaphthalene; alcohols such as ethanol, propanol or butanol; glycols and their ethers and esters such as propylene glycol or dipropylene glycol ether; ketones such as cyclohexanone, isophorone or diacetone alcohol; strongly polar solvents such as N-methyl-2-pyrrolidone, dimethyl sulfoxide or water; vegetable oils and their esters such as rapeseed oil, castor oil or soybean oil; and in some cases also silicone oils.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carriers are materials such as calcite or sand. In addition, innumerable pregranulated materials of inorganic or organic origin may be used, especially dolomite or pulverised plant residues.

Depending on the type of compound of formula I to be formulated, suitable surface-active compounds are nonionic, cationic and/or anionic surfactants having good emulsifying, dispersing and wetting properties. Surfactants will also be understood as comprising mixtures of surfactants.

Suitable anionic surfactants may be water-soluble soaps as well as water-soluble synthetic surface-active compounds.

Suitable soaps are the alkali metal salts, alkaline earth metal salts, ammonium salts or substituted ammonium salts of higher fatty acids ($C_{10}$–$C_{22}$), e.g. the sodium or potassium salts of oleic or stearic acid, or of natural fatty acid mixtures which can be obtained, inter alia from coconut oil or tallow oil. Further suitable soaps are also the fatty acid methyl taurin salts.

More often, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts, ammonium salts or substituted ammonium salts, and they contain a $C_8$–$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated or sulfonated fatty alcohol/ethylene oxide adducts. The sulfonated benzimidazole derivatives preferably contain 2 sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of an adduct of p-nonylphenol with 4 to 14 mol of ethylene oxide, or phospholipids, are also suitable.

Nonionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxylates, polyethoxylated castor oil, polyadducts of polypropylene and polyethylene oxide, tributylphenol polyethoxylate, polyethylene glycol and octylphenol polyethoxylate.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$–$C_{22}$alkyl radical and, as further substituents, optionally halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethylammonium bromide.

The surfactants customarily employed in the art of formulation are described, inter alia, in "Mc Cutcheon's Detergents and Emulsifiers Annual", Mc Publishing Corp., Ridgewood, N.J., 1981, H. Stache, "Tensid-Taschenbuch" (Handbook of Surfactants), Carl Hanser Verlag, Munich/Vienna 1981, and M. and J. Ash, "Encyclopedia of Surfactants", Vol I–III, Chemical Publishing Co., New York, 1980–81.

The herbicidal compositions will usually contain from 0.1 to 99% by weight, preferably from 0.1 to 95% by weight, of a combination of the compound of formula I with the compounds of formula II and/or III, from 1 to 99.9% by weight of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The formulations may also contain further ingredients such as stabilisers, vegetable oils or epoxidised vegetable oils, (epoxidised coconut oil, rapeseed oil or soybean oil), antifoams, typically silicone oil, preservatives, viscosity regulators, binders, tackifiers, as well as fertilisers or other chemical agents.

In particular, preferred formulations are made up as follows (throughout, percentages are by weight):

| Emulsifiable concentrates | |
| --- | --- |
| herbicidal combination: | 1 to 90%, preferably 5 to 20% |
| surfactant: | 1 to 30%, preferably 10 to 20% |
| liquid carrier: | 5 to 94%, preferably 70 to 85% |
| Dusts: | |
| herbicidal combination: | 0.1 to 10%, preferably 0.1 to 5% |
| solid carrier: | 99.9 to 90%, preferably 99.9 to 99% |
| Suspension concentrates: | |
| herbicidal combination: | 5 to 75%, preferably 10 to 50% |
| water: | 94 to 24%, preferably 88 to 30% |
| surfactant: | 1 to 40%, preferably 2 to 30% |
| Wettable powders: | |
| herbicidal combination: | 0.5 to 90%, preferably 1 to 80% |
| surfactant: | 0.5 to 20%, preferably 1 to 15% |
| solid carrier: | 5 to 95%, preferably 15 to 90% |
| Granulates: | |
| herbicidal combination: | 0.1 to 30%, preferably 0.1 to 15% |
| solid carrier: | 99.5 to 70%, preferably 97 to 85% |

The following Examples illustrate the invention without, however, limiting it in any way.

FORMULATION EXAMPLES

Combinations of the Compounds of Formulae I and II and/or III (throughout, percentages are by weight)

| F1. Emulsifiable concentrates | a) | b) | c) | d) |
| --- | --- | --- | --- | --- |
| combination of a compound of formula I and herbicides of formula II and/or III | 5% | 10% | 25% | 50% |
| calcium dodecylbenzenesulfonate | 6% | 8% | 6% | 8% |
| polyethoxylated castor oil (36 mol EO) | 4% | — | 4% | 4% |
| octylphenol polyethoxylate (7–8 mol EO) | — | 4% | — | 2% |
| cyclohexanone | — | — | 10% | 20% |
| mixture of aromatic hydrocarbons $C_9$–$C_{12}$ | 85% | 78% | 55% | 16% |

Emulsions of any desired concentration can be prepared by diluting such concentrates with water.

| F2. Solutions | a) | b) | c) | d) |
| --- | --- | --- | --- | --- |
| combination of a compound of formula I and herbicides of formula II and/or III | 5% | 10% | 50% | 90% |
| 1-methoxy-3-(3-methoxypropoxy)-propane | — | 20% | 20% | — |
| polyethylene glycol 400 | 20% | 10% | — | — |
| N-methyl-2-pyrrolidone | — | — | 30% | 10% |
| mixture of aromatic hydrocarbons $C_9$–$C_{12}$ | 75% | 60% | — | — |

The solutions are suitable for use as microdrops.

| F3. Wettable powders | a) | b) | c) | d) |
| --- | --- | --- | --- | --- |
| combination of a compound of formula I and herbicides of formula II and/or III | 5% | 25% | 50% | 80% |
| sodium ligninsulfonate | 4% | — | 3% | — |
| sodium laurylsulfate | 2% | 3% | — | 4% |
| sodium diisobutylnaphthalene sulfonate | — | 6% | 5% | 6% |
| octylphenol polyethoxylate (7–8 mol EO) | — | 1% | 2% | — |
| highly dispersed silica | 1% | 3% | 5% | 10% |
| kaolin | 88% | 62% | 35% | — |

The compound mixture is throughly mixed with the adjuvants and this mixture is ground in a suitable mill to give wettable powders which can be diluted with water to give suspensions of any desired concentration.

| F4. Coated granulates | a) | b) | c) |
| --- | --- | --- | --- |
| combination of a compound of formula I and herbicides of formula II and/or III | 0.1% | 5% | 15% |
| highly dispersed silica | 0.9% | 2% | 2% |
| inorganic carrier (Ø 0.1–1 mm) e.g. $CaCO_3$ or $SiO_2$ | 99.0% | 93% | 83% |

The compound mixture is dissolved in methylene chloride, the solution is sprayed on to the carrier, and the solvent is removed under vacuum.

| F5. Coated granulates | a) | b) | c) |
|---|---|---|---|
| combination of a compound of formula I and herbicides of formula II and/or III | 0.1% | 5% | 15% |
| polyethylene glycol 200 | 1.0% | 2% | 3% |
| highly dispersed silica | 0.9% | 1% | 2% |
| inorganic carrier (Ø 0.1–1 mm) e.g. CaCO₃ or SiO₂ | 98.0% | 92% | 80% |

The finely ground compound mixture is uniformly applied in a mixer to the kaolin moistened with polyethylene glycol. Non-dusty coated granulates are obtained in this manner.

| F6. Extruder granulates | a) | b) | c) | d) |
|---|---|---|---|---|
| combination of a compound of formula I and herbicides of formula II and/or III | 0.1% | 3% | 5% | 15% |
| sodium ligninsulfonate | 1.5% | 2% | 3% | 4% |
| carboxymethyl cellulose | 1.4% | 2% | 2% | 2% |
| kaolin | 97.0% | 93% | 90% | 79% |

The compound mixture is mixed with the adjuvants and the mixture is moistened with water. This mixture is extruded and then dried in a stream of air.

| F7. Dusts | a) | b) | c) |
|---|---|---|---|
| combination of a compound of formula I and herbicides of formula II and/or III | 0.1% | 1% | 5% |
| talcum | 39.9% | 49% | 35% |
| kaolin | 60.0% | 50% | 60% |

Ready for use dusts are obtained by mixing the compound mixture with the carriers on a suitable mill.

| F8. Suspension concentrates | a) | b) | c) | d) |
|---|---|---|---|---|
| combination of a compound of formula I and herbicides of formula II and/or III | 3% | 10% | 25% | 50% |
| ethylene glycol | 5% | 5% | 5% | 5% |
| nonylphenol polyethoxylate (15 mol EO) | — | 1% | 2% | — |
| sodium ligninsulfonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground compound mixture is homogeneously mixed with the adjuvants to give a suspension concentrate from which suspensions of any desired concentration can be prepared by dilution with water.

It is often more expedient to formulate the compound of formula I and the components of formula II and/or III individually and only to combine them shortly before application in the applicator in the desired mixture ratio as tank mixture in water.

BIOLOGICAL EXAMPLES
Example B1: Postemergence Test

In a greenhouse, monocot and dicot test plants are raised in plastic pots with standard soil. At the 4- to 6-leaf stage they are sprayed with an aqueous suspension of the test substances prepared from a 25% wettable powder (Example F3, b)) at a dosage of 2000 g a.i./ha (500 l water/ha). The test plants are then further cultivated in the greenhouse under optimum conditions. The test is evaluated after a test period of about 18 days (100%=total damage, 0%=no action). Valuations of 100 to 70% (in particular of 100 to 80%) signify good to excellent herbicidal action.

The novel compositions show a strong herbicidal action in this test. The same results are obtained by formulating the novel compositions in accordance with Examples F1 to F2 and F4 to F8.

What is claimed is:

1. A composition comprising an effective herbicidal amount of a compound of formula I

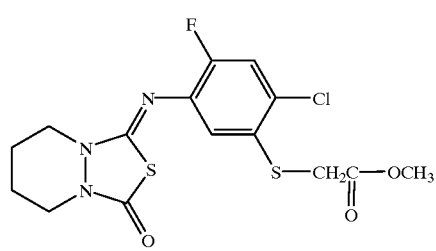

(I)

and a compound of formula II

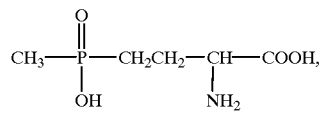

(II)

and/or of formula III

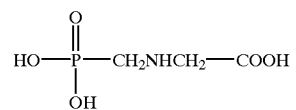

(III)

or an agriculturally acceptable salt of the compound of formula II and/or III in admixture, and an agriculturally acceptable carrier or diluent.

2. The composition according to claim 1, comprising the compound of formula I and the compound of formula II or III.

3. The composition according to claim 1, wherein the weight ratio of the compound of formula I to the compound of formula II and/or III is from 1:100 to 1:0.001.

4. A method of controlling undesirable plant growth in crops of cultivated plants, which comprises treating said plants or the locus thereof with the composition as claimed in claim 1.

5. A method according to claim 4, wherein the cultivated plants are cereals, rape, sugar beet, sugar cane, plantations, rice, cotton, maize or soybean.

6. A method according to claim 5, wherein the cultivated plant is maize or soybean.

7. The method according to claim 4, which comprises treating the cultivated plants or the locus thereof with the composition in rates of application corresponding to 0.25 to 2.5 kg of total compound per hectare.

8. The method according to claim 4 wherein the plants or locus thereof are treated postemergence with the composition.

9. A method of controlling undesirable plant growth in crops of cultivated plants which are tolerant or resistant to the compounds of formula II and/or III, which comprises treating said plants or the locus thereof with the composition as claimed in claim 1.

* * * * *